United States Patent [19]

Burdeska et al.

[11] 4,346,016
[45] Aug. 24, 1982

[54] 6-STYRYLQUINOXALINES, AND THEIR USE AS FLUORESCENT BRIGHTENERS

[75] Inventors: Kurt Burdeska, Basel; Guglielmo Kabas, Aesch, both of Switzerland

[73] Assignee: Ciba-Geigy Corporation, Ardsley, N.Y.

[21] Appl. No.: 254,822

[22] Filed: Apr. 16, 1981

[30] Foreign Application Priority Data

Apr. 23, 1980 [CH] Switzerland ............... 3130/80

[51] Int. Cl.³ .......................................... C07D 403/00
[52] U.S. Cl. ............... 252/301.22; 542/427; 542/447; 542/454; 544/353
[58] Field of Search .................. 252/301.22; 542/427, 542/447, 454

[56] References Cited

U.S. PATENT DOCUMENTS 3,684,729  8/1972  Tuite ..................................... 542/454
3,697,513 10/1972  Siegrist ............................ 252/301.22
4,184,977  1/1980  Eckstein et al. ................ 252/301.22

OTHER PUBLICATIONS

Manecke et al., Chem. Abstracts 80 (1974), #60236x.

Primary Examiner—Arthur P. Demers
Attorney, Agent, or Firm—Edward McC. Roberts

[57] ABSTRACT

6-Styrylquinoxalines of the formula

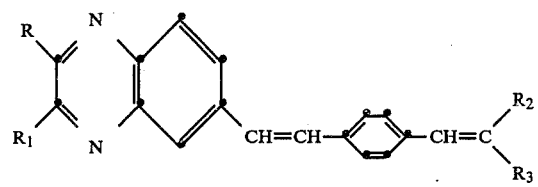

in which R and $R_1$ independently of one another are hydrogen, alkyl, aryl or aryloxy which is unsubstituted or substituted by non-chromophoric substituents, alkoxy, alkoxyalkoxy or phenylthio, $R_2$ is hydrogen or alkyl and $R_3$ is cyano or a group of the formula

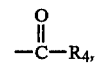

in which $R_4$ is alkoxy, alkoxyalkoxy, acyloxyalkoxy,

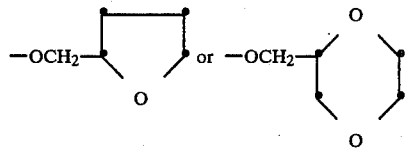

These new compounds are suitable for the fluorescent brightening of organic materials of high molecular weight, in particular for brightening polyester textiles and polyester spinning compositions.

10 Claims, No Drawings

6-STYRYLQUINOXALINES, AND THEIR USE AS FLUORESCENT BRIGHTENERS

The present invention relates to novel 6-styrylquinoxalines, a process for their preparation and their use for the fluorescent brightening of synthetic, regenerated man-made or natural organic materials of high molecular weight.

German Offenlegungsschrift No. 2,730,644 describes 6-styrylquinoxalines in which the styryl radical is unsubstituted or substituted by various heterocyclic ring systems.

The object of the present invention was thus to provide novel compounds which can be used as fluorescent brighteners and which give particularly useful white effects, and which have better exhaust properties and better fastness to light than the compounds of the state of the art.

It has been found that 6-styrylquinoxalines in which the styryl radical carries a vinyl substituent in the 4-position have these required properties, and in particular that they have a better affinity to the substrates to be brightened and that they are more productive than the comparable brightener systems known hitherto.

The novel 6-styrylquinoxalines have the formula

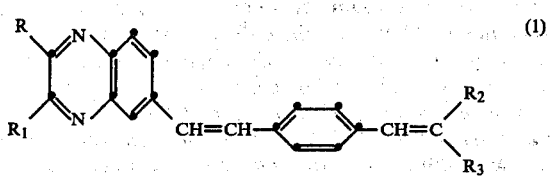

in which R and $R_1$ independently of one another are hydrogen, alkyl, aryl or aryloxy which is unsubstituted or substituted by non-chromophoric substituents, alkoxy, alkoxyalkoxy or phenylthio, $R_2$ is hydrogen or alkyl and $R_3$ is cyano or a group of the formula

in which $R_4$ is alkoxy, alkoxyalkoxy, acyloxyalkoxy,

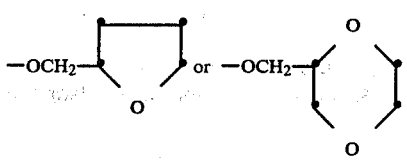

"Aryl" is preferably to be understood as meaning an aromatic mononuclear or polynuclear carbocyclic ring system, for example 1-naphthyl or 2-naphthyl, but in particular phenyl. The same definitions apply to the aryl part of the aryloxy substituents. The phenoxy radical is preferred.

Non-chromophoric substituents on aryl or aryloxy groups and hence also on phenyl or phenoxy groups are, for example, halogen, alkyl, hydroxyalkyl, halogenoalkyl, cyanoalkyl, alkoxyalkyl, phenylalkyl, carboxyalkyl, carbalkoxyalkyl, alkenyl, cycloalkyl, alkoxy, alkenyloxy, alkoxycarbonyl, aminocarbonyl, alkyl- or dialkyl-aminocarbonyl, cyano, alkylsulfonyl, alkoxysulfonyl, aminosulfonyl, hydroxyl, carboxyl or trifluoromethyl. In the abovementioned substituents, alkyl and alkoxy groups, including those in composite groups, for example alkoxyalkyl, each individually preferably have 1 to 6, in particular 1 to 4, carbon atoms. Cycloalkyl preferably has 5 or, in particular, 6, C atoms, and alkenyl has, in particular, 3 or 4 C atoms. The preferred halogen atoms are fluorine, chlorine and bromine, in particular chlorine. The aryl or aryloxy groups, or phenyl or phenoxy groups, can preferably contain one or two of the substituents mentioned. In the case of halogen, methyl and methoxy, the groups mentioned can also contain up to 3 substituents.

Substituted phenyl and phenoxy groups particularly preferably carry one or 2 substituents from the group comprising halogen (in particular chlorine), alkyl and/or alkoxy (preferably having in each case 1 to 4 C atoms, in particular methyl or methoxy).

Alkyl and alkoxy radicals R and $R_1$ preferably have 1 to 6, in particular 1 to 4, C atoms. The alkoxyalkoxy radical preferably has 3 to 10 C atoms. The alkoxyethoxy radical having preferably a total of 3 to 8, in particular 3 to 6, C atoms is particularly preferred. The same definition as given for the radicals R and $R_1$ applies to the alkoxy and alkoxyalkoxy radicals $R_4$. The acyloxyalkoxy group, which is preferably an alkanoyloxyalkoxy group ($-OR_x-OCO-R_y$), preferably has a total of 4 to 12, in particular 4 to 10 and especially 4 to 7, C atoms (the alkylene group $R_x$ in this group has 2 to 6, in particular 2 to 4 and preferably 2, C atoms and the alkyl group $R_y$ has 1 to 6, in particular 1 to 4, C atoms).

Preferred compounds of the formula (1) are those in which R and $R_1$ independently of one another are aryl or aryloxy which is unsubstituted or substituted by nonchromophoric substituents, or alkoxy, alkoxyalkoxy or phenylthio.

Compounds which are of interest in practice are, in particular, those of the formula

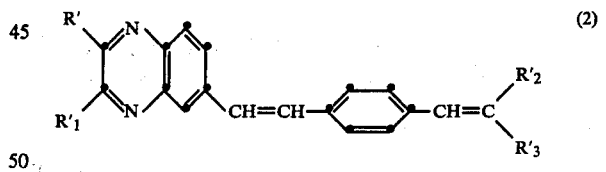

in which R' and $R_1'$ independently of one another are phenyl or phenoxy which is unsubstituted or substituted by one or two substituents from the group comprising halogen and alkyl and alkoxy having in each case 1 to 4 C atoms, or are alkoxy having 1 to 4 C atoms, alkoxyethoxy having 3 to 6 C atoms or phenylthio, $R_2'$ is hydrogen or alkyl having 1 to 4 C atoms and $R_3'$ is cyano or a group of the formula

in which $R_4'$ is alkoxy having 1 to 4 C atoms, alkoxyethoxy having 3 to 6 C atoms, alkanoyloxyethoxy having 4 to 7 C atoms,

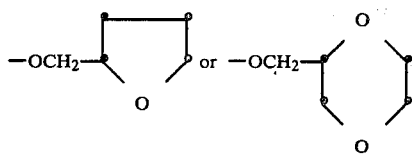

Preferred 6-styrylquinoxalines are those of the formula

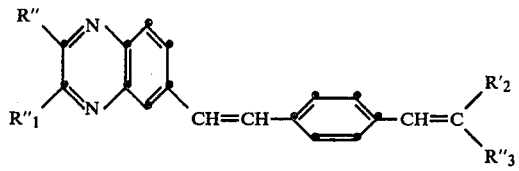

in which R" and $R_1$" independently of one another are alkoxy having 1 to 4 C atoms, alkoxyethoxy having 3 to 6 C atoms, phenyl or phenoxy, $R_2'$ is hydrogen or alkyl having 1 to 4 C atoms and $R_3$" is cyano or alkoxycarbonyl having 2 to 5 C atoms.

The 6-styrylquinoxalines of the formula (1) and of the subordinate formulae according to the invention can be prepared by a process which comprises subjecting a compound of the formula

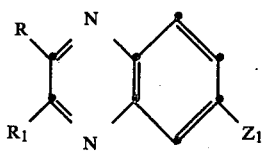

to a condensation reaction with a compound of the formula

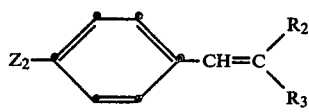

in which R, $R_1$, $R_2$ and $R_3$ are as defined under formula (1) and one of the two symbols $Z_1$ and $Z_2$ is the group

and the other is a grouping of the formula

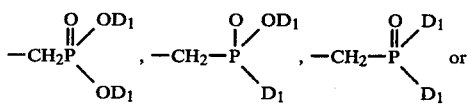

in which $D_1$ is an unsubstituted or substituted alkyl, aryl, cycloalkyl or aralkyl radical, in an organic solvent and in the presence of basic condensing agents. $D_1$ is preferably an alkyl radical having 1 to 6 C atoms, a phenyl or benzyl radical which is unsubstituted or substituted by chlorine or alkyl having 1 to 4 C atoms, or the cyclohexyl radical; a grouping of the formula

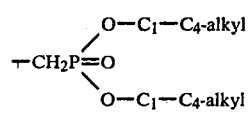

is particularly preferred.

In compounds of the formula (5), $Z_2$ is preferably the formyl radical.

Solvents used are advantageously inert solvents, for example hydrocarbons, such as toluene or xylene, or alcohols, such as methanol, ethanol, isopropanol, butanol, glycols, glycol ethers, such as 2-methoxyethanol, hexanol, cyclohexanol or cyclooctanol, and also ethers, such as diisopropyl ether, dioxane or tetrahydrofuran, and furthermore formamides or N-methylpyrrolidone. Dipolar organic solvents, such as dimethylformamide and dimethylsulfoxide, are particularly suitable.

Condensing agents are strongly basic compounds, for example alkali metal hydroxides, amides and alcoholates and alkaline earth metal hydroxides, amides and alcoholates, for example potassium hydroxide, sodium hydroxide, potassium tert.-butylate, sodium amide or sodium methylate, as well as alkali metal compounds of dimethylsulfoxide, and alkali metal hydrides, and in some cases alkali metal dispersions.

The reaction is preferably carried out in a temperature range from 0° to 100° C. The compounds according to the invention are also obtained by a process which comprises using the corresponding quaternary phosphonium salts, for example the triphenylphosphonium salts, in place of the phosphone compounds (4) or (5), and subjecting these salts to a condensation reaction with the aldehydes (5) or (4) respectively, via the phosphorylene stage.

Further conversions which are known per se can be carried out on the reaction products of the formula (1) obtained by the above process. Thus, compounds of the formula (1) in which $R_3$ is a group of the formula

in which $R_4$ is alkoxyalkoxy (in particular alkoxyethoxy, acyloxyalkoxy (in particular alkanoyloxyethoxy),

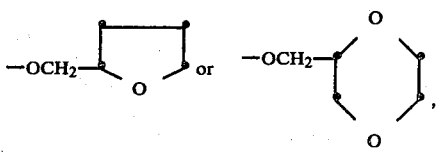

are thus preferably prepared by a process which comprises using a compound of the formula (5) in which $R_4$ is alkoxy; the resulting compound of the formula (1) in which $R_4$ is alkoxy can then be converted into those compounds in which $R_4$ is as defined above by the generally known trans-esterification with corresponding alcohols. For example, compounds of the formula (1) in which $R_4$ is methoxy can be reacted with alcohols of the formulae $HOCH_2CH_2$—O—alkyl,

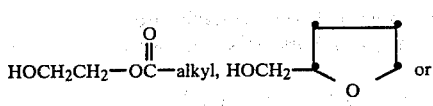

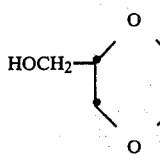 or

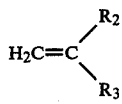

in a manner which is known per se, and the corresponding compounds of the formula (1) in which $R_4$ is as defined above are then obtained. The said trans-esterification reactions can, of course, also already have been carried out on the starting compounds of the formula (5) in which $R_3$ is an alkoxycarbonyl group. Compounds of the formula (5) in which $R_3$ includes all definitions given under formula (1) are then obtained.

The starting materials of the formulae (4) and (5) are known, or they can be prepared by processes which are known per se. Quinoxalines of the formula (4) are described, for example, in German Offenlegungsschrift No. 2,730,644, or can easily be prepared by the processes mentioned in that publication. The compounds of the formula (5) in which $R_3$ is alkoxycarbonyl are described in the literature. Other compounds of the formula (5) in which $R_3$ is another ester grouping can be prepared by appropriate known trans-esterification reactions (see above). Compounds of the formula (5) in which $R_3$ is cyano are described in U.S. patent application Ser. No. 214,946, or they can be obtained by a process analogous to those described therein (see also Example 2, preparation of the starting material).

Alternatively, the starting compounds of the formula (5) can also be prepared by a process which comprises reacting a compound of the formula

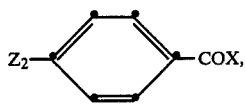

in which X is chlorine, bromine or iodine, with a compound of the formula

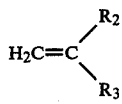

in the presence of a base and a Pd(O)-complex catalyst or of a catalyst of the formula Pd(X')$_2$, in which X' is chlorine, bromine, iodine, cyano, —NO$_3$, C$_{1-12}$—alkyl—COO— or CH$_3$COCHCOCH$_3$, or of a Pd(II)-complex catalyst. The process is preferably carried out with the aid of PdCl$_2$, Pd acetylacetonate or Pd acetate as the catalyst, at temperatures between 0° and 200° C., in an inert solvent, preferably anisole, toluene or xylene (see also Example 3).

Compounds of the formula (1) can, however, also be prepared by other processes which are known per se. Thus, a Schiff's base of the formula

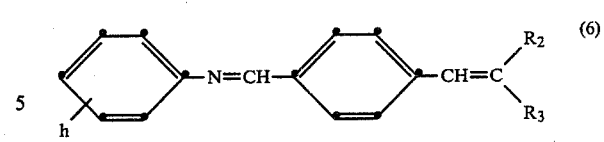

in which $R_2$ and $R_3$ are as defined above and h is advantageously hydrogen or chlorine, can be reacted with a methyl compound of the formula

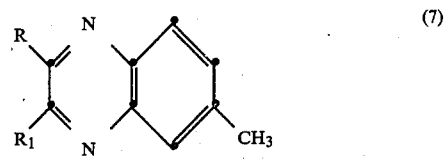

in which R and $R_1$ are as defined above, in the presence of a strongly basic alkali metal compound, in dimethylformamide as the reaction medium. Strongly basic alkali metal compounds are to be understood here as those alkali metal compounds which have a base strength of at least approximately that of lithium hydroxide. These compounds can be, for example, alcoholates or hydroxides of lithium, sodium, potassium, rubidium or caesium, or strongly basic ion exchangers. Potassium compounds of the formula $$KOC_{m-1}H_{2m-1}$$

in which m is an integer from 1 to 6, for example potassium hydroxide or potassium tert.-butylate, are advantageously used. In the case of alkali metal alcoholates, the reaction is to be carried out in a virtually anhydrous medium, whilst water contents of up to 25% (for example water of crystallisation) are permitted in the case of alkali metal hydroxides. A water content of up to about 10% has proved advantageous in the case of potassium hydroxide. Examples of other alkali metal compounds which can be used are: sodium methylate, sodium hydroxide, lithium hydroxide, rubidium hydroxide, caesium hydroxide and the like. It is of course also possible to carry out the reaction with mixtures of such bases.

The compounds of the formula (7) are advantageously reacted with the Schiff's base of the formula (6) in equivalent amounts, so that a substantial excess of neither component is present. At least the equivalent amount of the alkali metal compound is advantageously used, i.e. at least 1 mol of a compound with, for example, one KO group per mol of Schiff's base. In the case of potassium hydroxide, 4 to 8 times the amount is preferably used. The reaction can generally be carried out at temperatures in the range from about 10° to 150° C. If alcoholates are used as the potassium compound in the reaction, it is generally unnecessary to supply heat. Thus, the procedure followed comprises adding the Schiff's base of the formula (6) to a mixture of the compound of the formula (7), the solvent and the potassium alcoholate, advantageously while stirring and in the absence of air, at a temperature between 15° and 30° C., after which the reaction takes place by itself, the temperature rising slightly. If potassium hydroxide is used, it is frequently necessary to carry out the reaction at a higher temperature. For example, the reaction mixture is warmed slowly to 30° to 100° C. and is then kept at this temperature for some time, for example ½ to 2 hours. The end products can be isolated from the reaction mixtures by customary methods which are known per se.

The Schiff's bases of the formula (6) can easily be obtained by reacting aldehyde compounds of the formula (5) with a substituted or unsubstituted aniline in a known manner. The methyl compounds of the formula (7) are known (see, for example, German Offenlegungsschrift No. 2,730,644), or they can be obtained by the process described in that publication.

The compounds according to the invention exhibit a pronounced fluorescence in solution or in the finely divided state. They are used, according to the invention, for optically brightening a wide variety of synthetic, regenerated man-made or natural organic materials of high molecular weight.

Without any restriction being implied by the following classification, the following groups are examples of organic materials which can be optically brightened:

I. Synthetic organic materials of high molecular weight:
   (a) Polymerization products based on organic compounds containing at least one polymerisable carbon-carbon double bond, i.e. their homopolymers or copolymers as well as their after-treatment products, for example crosslinking, grafting or degradation products, polymer blends, or products obtained by modification of reactive groups, for example polymers based on $\alpha,\beta$-unsaturated carboxylic acids or derivatives of such carboxylic acids, especially on acrylic compounds (for example acrylates, acrylic acid, acrylonitrile, acrylamides and their derivatives or their methacrylic analogues), on olefin hydrocarbons (for example, ethylene, propylene, styrenes or dienes and also so-called ABS polymers), and polymers based on vinyl and vinylidene compounds (for example vinyl chloride, vinyl alcohol and vinylidene chloride),
   (b) Polymerisation products which can be obtained by ring opening, for example polyamides of the polycaprolactam type, and also polymers which are obtained both by polyaddition and by polycondensation, for example polyethers or polyacetals,
   (c) Polycondensation products or precondensates based on bifunctional or polyfunctional compounds with condensable groups, the homocondensation and co-condensation products and after-treatment products thereof, for example polyesters, in particular saturated polyesters (for example polyesters of ethylene glycol terephthalic acid) or unsaturated polyesters (for example maleic acid-dialcohol polycondensates and their crosslinking products with copolymerisable vinyl monomers), unbranched and branched polyesters (also including those based on polyhydric alcohols, for example alkyd resins), polyamides (for example hexamethylenediamine adipate), maleic resins, melamine resins, the precondensates and analogues thereof, polycarbonates and silicones,
   (d) Polyaddition products, such as polyurethanes (crosslinked and uncrosslinked) and epoxide resins.

II. Regenerated man-made organic materials, for example cellulose esters of varying degrees of esterification (so-called 2½-acetate or triacetate) or cellulose ethers, regenerated cellulose (viscose or cuprammonium cellulose), or their after-treatment products, and casein plastics.

III. Natural organic materials of animal or vegetable origin, for example based on cellulose or proteins, such as cotton, wool, linen, silk, varnish gums, starch and casein.

The organic materials to be optically brightened can be in the most diverse states of processing (raw materials, semi-finished goods or finished goods). On the other hand, they can be in the form of structures of the most diverse shapes, for example predominantly three-dimensionally expanded bodies, such as sheets, profiles, injection mouldings, various machined articles, chips, granules or foams, and also predominantly two-dimensionally shaped bodies, such as films, foils, lacquers, coverings, impregnations and coatings, or predominantly one-dimensionally shaped bodies, such as filaments, fibres, flocks and wires. The said materials can, on the other hand, also be in unshaped states, in the most diverse homogeneous or inhomogeneous forms of division, for example in the form of powders, solutions, emulsions, dispersions, latices, pastes or waxes.

Fibrous materials can be, for example, in the form of endless filaments (stretched or unstretched), staple fibres, flocks, hanks, textile filaments, yarns, threads, non-wovens, felts, waddings, flocked structures or woven textile or bonded textile fabrics, knitted fabrics and papers, cardboards or paper pulps.

The compounds to be used according to the invention are of importance, inter alia, for the treatment of organic textile materials, especially woven textile fabrics. If fibres, which can be in the form of staple fibres or endless filaments or in the form of hanks, woven fabrics, knitted fabrics, fleeces, flocked substrates or bonded fabrics, are to be optically brightened according to the invention, this is advantageously effected in an aqueous medium, wherein the compounds in question are present in a finely divided form (suspensions, so-called microdispersions, or in some cases solutions). If desired, dispersants, stabilisers, wetting agents and further assistants can be added during the treatment.

Depending on the type of brightener compound used, it can be advantageous to carry out the treatment in a neutral or alkaline or acid bath. The treatment is usually carried out at temperatures between about 20° and 140° C., for example at the boiling point of the bath or near it (about 90° C.). Solutions or emulsions in organic solvents can also be used for the finishing, according to the invention, of textile substrates, as is practised in the dyeing industry in so-called solvent dyeing (padthermofixation, or exhaust dyeing processes in dyeing machines).

The novel fluorescent brighteners of the present invention can further be added to, or incorporated in, the materials before or during their shaping. Thus they can for example be added to the compression moulding composition or injection moulding composition during the manufacture of films, sheets (for example by incorporating into polyvinyl chloride in a roll mill at elevated temperature) or mouldings.

If the fashioning of man-made synthetic or regenerated man-made organic materials is effected by spinning processes or from spinning compositions, the fluorescent brighteners can be applied by the following processes:

addition to the starting substances (for example monomers) or intermediates (for example precondensates or prepolymers), i.e. before or during the polymerisation, polycondensation or polyaddition, sprinkling in powder form on polymer chips or granules for spinning compositions, bath dyeing of polymer chips or granules for spinning compositions, metered addition to spinning melts or spinning solutions, and application to the spun tow before stretching.

The novel optical brighteners of the present invention can, for example, also be employed in the following use forms:

(a) in mixtures with dyes (shading) or pigments (coloured pigments or especially, for example, white pigments), or as an additive to dyebaths, printing pastes, discharge pastes or reserve pastes, or for the aftertreatment of dyeings, prints or discharge prints, (b) in mixtures with carriers, wetting agents, plasticisers, swelling agents, antioxidants, light stabilisers, heat stabilisers and chemical bleaching agents (chlorite bleach or bleaching bath additives), (c) in mixtures with crosslinking agents or finishing agents (for example starch or synthetic finishes), and in combination with a wide variety of textile finishing processes, especially resin finishes (for example creaseproof finishes such as wash-and-wear, permanent-press or non-iron), as well as flameproof finishes, soft-handle finishes, anti-soiling finishes or antistatic finishes, or antimicrobial finishes, (d) incorporation of the fluorescent brightener into polymeric carriers (polymerisation, polycondensation or polyaddition products) in dissolved or dispersed form, for use, for example, in coating agents, impregnating agents or binders (solutions, dispersions and emulsions) for textiles, non-wovens, paper and leather, (e) as additives to master batches, (f) as additives to a wide variety of industrial products in order to render these more marketable (for example improving the appearance of soaps, detergents, pigments), (g) in combination with other fluorescent brightening substances, (h) in spinning bath preparations, i.e. as additives to spinning baths which are used for improving the slip for the further processing of synthetic fibres, or from a special bath before the stretching of the fibre, (i) as scintillators or for various purposes of a photographic nature, for example for electrophotographic reproduction or supersensitising, (j) depending on the substitution, as laser dyes, for example for use in testing materials (defectoscopy).

If the brightening process is combined with textile treatment or finishing methods, the combined treatment can in many cases advantageously be carried out with the aid of appropriate stable preparations which contain the fluorescent brightener compounds in such a concentration that the desired white effect is achieved.

In certain cases, the fluorescent brighteners are made fully effective by an after-treatment. This can be, for example, a chemical treatment (for example acid treatment), a thermal treatment or a combined chemical/thermal treatment. Thus, for example, the appropriate procedure to follow in brightening a number of fibre substances, for example polyester fibres, with the brighteners according to the invention is to impregnate these fibres with the aqueous dispersions (or in some cases also solutions) of the brighteners at temperatures below 75° C., for example at room temperature, and to subject them to a dry heat treatment at temperatures above 100° C., it being generally advisable additionally to dry the fibrous material beforehand at a moderately elevated temperature, for example at not less than 60° C. to about 130° C. The heat treatment in the dry state is then advantageously carried out at temperatures between 120° and 225° C., for example by heating in a drying chamber, by ironing within the specified temperature range or by treatment with dry, superheated steam. The drying and dry heat treatment can also be carried out in immediate succession or combined in a single operation.

The amount of novel fluorescent brightener to be used according to the invention, based on the weight of the material to be brightened, can vary within wide limits. A marked and lasting effect can be obtained even with very insignificant amounts, in certain cases, for example, 0.0001 percent by weight. But it is also possible to use amounts of up to about 0.8 percent by weight and, on occasion, up to about 2 percent by weight. For most practical purposes, it is preferable to use amounts between 0.0005 and 0.5 percent by weight.

For various reasons it is often advantageous not to use the brighteners by themselves, i.e. pure, but in admixture with a wide variety of assistants and extenders, for example anhydrous sodium sulfate, sodium sulfate decahydrate, sodium chloride, sodium carbonate, alkali metal phosphates, such as sodium or potassium orthophosphate, sodium or potassium pyrophosphate and sodium or potassium tripolyphosphates or alkali metal silicates.

The novel fluorescent brighteners are also particularly suitable for use as additives to wash liquors or heavy duty and domestic detergents, to which they can be added in various ways. They are advantageously added to wash liquors in the form of their solutions in water or organic solvents, or, in a finely divided form, as aqueous dispersions. They are advantageously added to domestic or heavy duty detergents in any stage of the manufacturing process of the detergents, for example to the slurry before the washing powder is atomised, or during the preparation of liquid detergent combinations. They can be added either in the form of a solution or dispersion in water or other solvents or, without assistance, as a dry brightening powder. For example, the brighteners can be mixed, kneaded or ground with the active detergents and, in this form, admixed with the finished washing powder. However, they can also be sprayed in a dissolved or pre-dispersed form onto the finished detergent.

Suitable detergents are the known mixtures of active detergents, for example soaps in the form of chips and powders, synthetics, soluble salts of sulfonic acid hemiesters of higher fatty alcohols, higher and/or multiple alkyl substituted arylsulfonic acids, sulfocarboxylic acid esters of medium to higher alcohols, fatty acid acylaminoalkyl- or acylaminoaryl-glycerol sulfonates and phosphoric acid esters of fatty alcohols. Suitable builders which can be used are, for example, alkali metal polyphosphates and polymetaphosphates, alkali metal pyrophosphates, alkali metal salts of carboxymethylcellulose and other soil redeposition inhibitors, and also alkali metal silicates, alkali metal carbonates, alkali metal borates, alkali metal perborates, nitrilotriacetic acid, ethylenediaminotetraacetic acid, and foam stabilisers, such as alkanolamides of higher fatty acids. The detergents can further contain for example: antistatic agents, fat restorative skin protectives, such as lanolin, enzymes, antimicrobial agents, perfumes and colorants.

The novel fluorescent brighteners have the particular advantage that they are also active in the presence of active chlorine donors, for example hypochlorite, and can be used without significant loss of effect in wash liquors containing non-ionic washing agents, for example alkylphenolpolyglycol ethers.

The compounds according to the invention are added in amounts of 0.005 to 1% or more, based on the weight of the finished detergent in liquid or powder form. Wash liquors which contain the indicated amounts of the claimed fluorescent brighteners impart a brilliant appearance in daylight when used to wash textiles made from cellulose fibres, polyamide fibres, resin-finished cellulose fibres, polyester fibres, wool etc.

The washing treatment is carried out, for example, as follows:

The textiles are treated for 1 to 30 minutes at 20° to 100° C. in a wash liquor which contains 1 to 10 g/kg of a built-up composite detergent and 0.05 to 1%, based on the weight of the detergent, of the claimed brighteners. The liquor ratio can be 1:3 to 1:50. After they have been washed, the textiles are rinsed and dried in the usual manner. The wash liquor can contain 0.2 g/l of active chlorine (for example as hypochlorite) or 0.1 to 2 g/l of sodium perborate as a bleaching agent.

Particularly preferred fields of use for the compounds according to the invention are the following: fluorescent brightening of polyesters, and in particular both of polyester fibres and fabrics by the exhaust method or pad-thermofix method and of polyester spinning compositions. Polyester-cotton blends or polyester-wool blends are also whitened in a very advantageous manner with the aid of the compounds according to the invention. Further substrates which can be whitened with the aid of the compounds of the formula (1) are: polyamide fabric, cellulose acetate fabric and polystyrene and polyvinyl chloride moulding compositions. However, the compounds are particularly preferably used for the fluorescent brightening of polyester fibres by the exhaust method or pad-thermofix method or of polyester spinning compositions. The compounds according to the invention are distinguished by a particularly good affinity to the substrates to be brightened.

The following examples illustrate the preparation of the compounds according to the invention and their use in more detail. In these examples, as in the remainder of the description, percentages and parts are always by weight, unless otherwise stated. Unless indicated to the contrary, melting points and boiling points are uncorrected.

EXAMPLE 1

13.61 g of 2,3-dimethoxy-6-diethoxy-phosphoryl-methyl-quinoxaline and 6.3 g of 4-formylcinnamonitrile are dissolved in 100 ml of dimethylformamide. 2.5 g of sodium methylate are then introduced into the solution in small portions in the course of 15 minutes. The reaction mixture is stirred for a further 30 minutes at room temperature and then for a further 2 hours at 40°–45° C. It is stirred into 800 ml of ice-water and rendered acid with formic acid, and the solid is filtered off and washed with water and methanol. After drying, 11.6 g of the compound of the formula

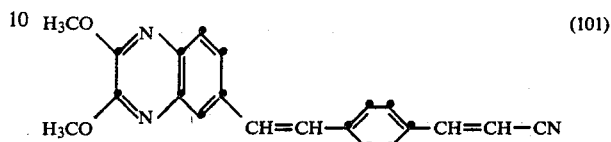 (101)

are obtained.

The product crystallises from xylene, with the addition of bleaching earth, in yellow crystals having a melting point of 227°–228° C.

If the corresponding phosphonates are used as starting materials, the compounds of the general formula

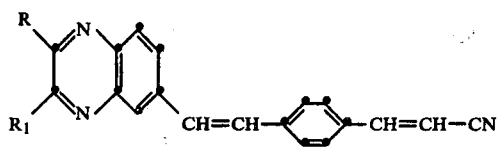

listed in Table I which follows are obtained in an analogous manner.

TABLE I

| Compound No. | R | R₁ | Melting point (°C.) |
|---|---|---|---|
| 102 | —OC₃H₇ | —OC₃H₇ | 152–154 |
| 103 | —OCH₃ | —OC₃H₇ | 140–142 |
| 104 | 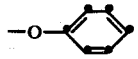 | 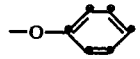 | 220–221 |
| 105 |  |  | 256–257 |

EXAMPLE 2

15 g of 2.3-di-(2-methoxy-ethoxy)-6-diethoxyphosphorylmethylquinoxaline and 5.5 g of 4-formylcinnamonitrile are dissolved in 80 ml of dimethylformamide. 2.45 g of solid sodium methylate are introduced into the solution in the course of 20 minutes. The mixture is then stirred for a further 30 minutes at room temperature and then, in order to bring the reaction to completion, for a further 2 hours at 40°–45° C. After cooling the mixture to room temperature, it is rendered acid with formic acid and the resinous product which has precipitated is separated off from the aqueous phase. After drying, 13.5 g of a mixture of the compounds of the formulae

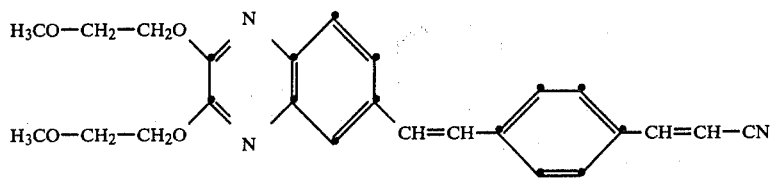

(201)

(Melting point: 117°-118° C.) and

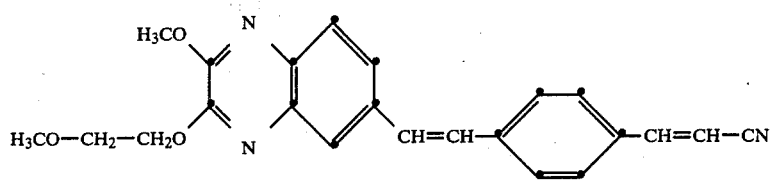

(202)

(Melting point: 169°-171° C.) are obtained.

The two compounds are separated by column chromatography on silica gel. Solvent and mobile phase: toluene/ethyl acetate in the ratio 80:20.

The 4-formylcinnamonitrile required as the starting material in Examples 1 and 2 can be obtained as follows:

148 g of terephthalaldehyde, 85 g of cyanoacetic acid and 3 g of ammonium acetate are added to 200 ml of toluene and 100 ml of pyridine in a reflux apparatus, which is provided with a Barrett trap to remove the water which has condensed out of the refluxing vapours. The reaction mixture is warmed and is kept simmering under reflux, with stirring, until no further water is formed (about 2-3 hours).

After adding 200 ml of water, the mixture is subjected to steam distillation, during which toluene and other volatile substances are removed. The residue is then stirred vigorously with a solution of 300 g of sodium bisulfite in 900 ml of water at 50° C., cooled to room temperature and filtered. The filtrate is treated with 600 ml of 30% aqueous formaldehyde solution and the aldehyde which has separated out is taken up in toluene. The toluene solution is dried over magnesium sulfate, the toluene is evaporated off and the 4-formylcinnamonitrile is distilled.

84.5 g of the E/Z-isomer mixture of boiling point 132°-155° C./13,332 Pa are obtained, from which the E-form of melting point 118°-119° C. is obtained by crystallisation from methanol.

EXAMPLE 3

10.2 g of 2,3-dimethoxy-6-diethoxy-phosphorylmethyl-quinoxaline and 5.13 g of 2-methyl-3-(4-formylphenyl)-2-propenonitrile (melting point: 63°-64° C.) are dissolved in 80 ml of dimethylformamide. 2.1 g of solid sodium methylate are now introduced in small portions at room temperature in the course of about 20 minutes. During this addition, the temperature rises to about 35° C. The reaction mixture is then stirred for a further 2 hours at 40°-45° C. After cooling to room temperature, the mixture is rendered acid with formic acid and the product which has precipitated is filtered off, washed with water and with methanol and dried at 70° C. in vacuo. 9.8 g of the compound of the formula

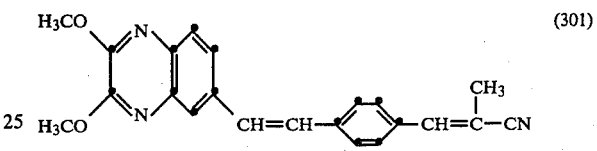

(301)

are obtained in the form of yellow-brown crystals. The product crystallises from toluene, with the addition of bleaching earth, in yellow crystals having a melting point of 182°-183° C.

The 2-methyl-3-(4-formylphenyl)-2-propenonitrile used as the starting material can be prepared as follows:

360 g of a 30% solution of sodium methylate in methanol are added dropwise to a suspension of 134 g of terephthalaldehyde in 500 ml of methanol at 20°-25° C. 191 g of 2-(diethylphosphoryl)-propionitrile [prepared by the method of M. L. Raggio and D. S. Watt, J. Org. Chem. 41, 1873 (1976)] are now slowly added dropwise to the resulting reaction solution at 20°-25° C. The reaction mixture is stirred at room temperature for 6 hours and then poured onto 1,000 ml of water, and the aqueous suspension is adjusted to a pH value of 7 with acetic acid. The product which has precipitated is filtered off, dried and then chromatographed on silica gel. 35 g (20.5% of theory) of 2-methyl-3-(4-formylphenyl)-2-propenonitrile of the formula

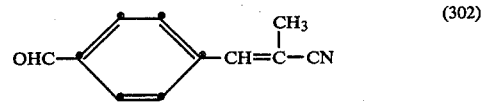

(302)

and then obtained in the form of colourless crystals having a melting point of 63°-64° C.

The procedure described above is repeated, using an equivalent amount of ethyl 2-(diethylphosphoryl)propionate in place of 2-(diethylphosphoryl)-propionitrile. The compound of the formula

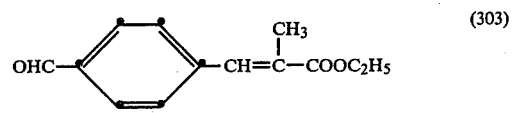

(303)

having a boiling point of 127°-131° C. under 7 Pa is obtained.

Alternatively, the starting compound of the formula (302) can also be prepared as follows:

3.49 g of 4-formylbenzoyl chloride together with 2.09 g of methacrylonitrile, 5.79 g of tri-n-butylamine, 50 ml of p-xylene and 0.0561 g of palladium acetate are introduced into a 100 ml glass flask and the mixture is warmed to 120° C., with stirring. Slight evolution of gas can be observed. After a stirring time of 2 hours, the contents of the flask are cooled and are twice extracted by shaking with 25 ml of 2 N hydrochloric acid each time. The xylene phase is dried with magnesium sulfate and distilled. After distilling off the xylene, 1.35 g of the compound of the formula (302) are obtained as a 60:40 Z/E mixture having a melting point of 63°–64° C.

The procedure described above is repeated, except that the equivalent amount of ethyl methacrylate is used in place of methacrylonitrile, affording the compound of the formula (303) in a yield of 29.4% of theory and having a melting point of 127°–131° C. under 7 Pa.

EXAMPLE 4

2.3 g of solid sodium methylate are introduced into a solution of 13.87 g of 2,3-dipropoxy-6-diethoxy-phosphorylmethyl-quinoxaline and 6.7 g of methyl 4-formylcinnamate in 80 ml of dimethylformamide in the course of 15 minutes. The reaction mixture is stirred for a further 30 minutes at room temperature and then for a further 2 hours at 40°–45° C. After cooling to room temperature, the mixture is rendered acid with formic acid and stirred into 800 ml of ice-water. The product which has precipitated is filtered off, washed with water and methanol and dried at 80° C. in vacuo. 12 g of the compound of the formula

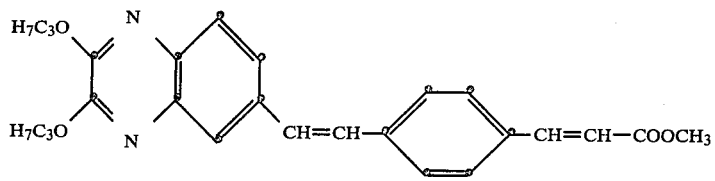

(401)

are obtained. The product crystallises from a mixture of cyclohexane/toluene in the ratio 4:1, with the addition of bleaching earth, in greenish-tinged yellow crystals having a melting point of 161°–162° C.

The 2,3-dipropoxy-6-diethoxy-phosphorylmethyl-quinoxaline required as the starting material is prepared in a known manner by side chain bromination of 2,3-dipropoxy-6-methyl-quinoxaline and reaction of the resulting 2,3-dipropoxy-6-bromomethyl-quinoxaline (melting point: 83°–84° C.) with triethyl phosphite.

The compounds of the general formula

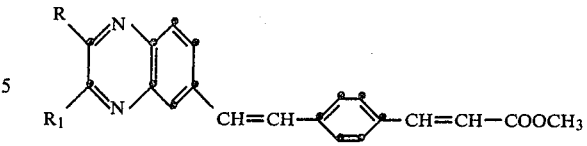

listed in Table II which follows are obtained by a method analogous to that described in Example 4, using the corresponding phosphonates as starting materials.

TABLE II

| Compound No. | R | $R_1$ | Melting point (°C.) |
|---|---|---|---|
| 402 | —OCH₃ | —OCH₃ | 186–187 |
| 403 | —OCH₂—CH₂—OCH₃ | —OCH₂—CH₂—OCH₃ | 138–139 |
| 404 | ⌬ | ⌬ | 218–219 |
| 405 | —O—⌬ | —O—⌬ | 248–249 |

EXAMPLE 4a 10.9 g of 2,3-dimethoxy-6-formyl-quinoxaline and 16.3 g of ethyl 4-diethoxy-phosphorylmethylcinnamate are dissolved in 160 ml of dimethylformamide. A solution of 1.4 g of sodium in 20 ml of anhydrous ethanol is then allowed to run into this solution in the course of 20 minutes, with stirring and cooling. The mixture is stirred for a further hour at room temperature and then for a further 2½ hours at 40°–45° C. After cooling to room temperature, the reaction mixture is rendered weakly acid with formic acid and the product which has precipitated is filtered off, washed with water and methanol and dried. 17.5 g of the compound of the formula

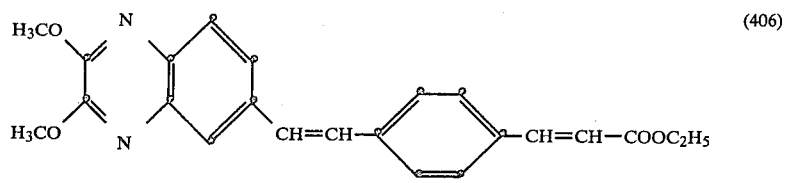

(406)

are obtained. The product is recrystallised first from ethylene glycol monomethyl ether and then from xylene in the presence of bleaching earth. The compound of the formula (406) is then obtained in the form of slightly yellow crystals having a melting point of 158°–160° C.

EXAMPLE 5

A polyester fabric (Terylene type 540) is treated, as a liquor ratio of 1:20, on a dyeing apparatus, with an aqueous bath containing 0.1% (based on the weight of fabric) of the compound of the formula (101), (102), (201), (202) or (301), 1 g/liter of the condensation product of 35 mols of ethylene oxide and 1 mol of stearyl alcohol. The bath is now warmed from 40° to 120° C. in the course of 30 minutes and is kept at this temperature for 30 minutes and then cooled to 15° C. in the course of 15 minutes. The fabric is then rinsed in running, deionised water and dried at 70° C. The polyester fabric treated in this manner has a good white effect.

EXAMPLE 6

A polyester fabric (Terylene type 540) is padded, at room temperature, with a liquor containing 1 g of the compound of the formula (402), (403), (301), (405) or (404) and 1 ml of the condensation product of 8–9 mols of ethylene oxide and 1 mol of p-tert.-octylphenol per liter. The liquor pick-up is 80%. The fabric is then dried at 80° C. for 10 minutes and subjected to thermofixing at 200° C. for 30 seconds. The fabric treated in this manner has a good white effect.

EXAMPLE 7

A polyester/cotton mixed fabric is treated, on a dyeing apparatus, at a liquor ratio of 1:20, with an aqueous bath containing 0.1%, based on the weight of fabric, of the compound of the formula (102), (103), (201), (301) or (403) and 1 g/liter of the condensation product of 35 mols of ethylene oxide and 1 mol of stearyl alcohol. The bath is now warmed from 40° to 97° C. in the course of 30 minutes and is kept at this temperature for 30 minutes and then cooled to 15° C. in the course of 15 minutes. The fabric is then rinsed with running, deionised water and dried at 70° C. The polyester/cotton mixed fabric treated in this manner is distinguished by a good white effect.

EXAMPLE 8

A polyamide-6,6 warp-knit fabric is treated, on a dyeing apparatus, at a liquor ratio of 1:20, with an aqueous bath containing 0.2%, based on the weight of fabric, of the compound of the formula (101), (102), (201), (202) or (401) and 3 g/liter of a mixture of 60 parts by weight of sodium hyposulfite and 40 parts by weight of sodium pyrophosphate. The bath is warmed from 40° to 130° C. in the course of 30 minutes and is kept at this temperature for 30 minutes and then cooled to 15° C. in the course of 15 minutes. The fabric is then rinsed in running, deionised water and dried at 60° C. The polyamide fabric treated in this manner has a good white effect.

EXAMPLE 9

A triacetate fabric is treated, on a dyeing apparatus, at a liquor ratio of 1:20, with an aqueous bath containing 1.0%, based on the weight of fabric, of the compound of the formula (101), (201), (202), (301) or (402) and 1 g/liter of the condensation product of 35 mols of ethylene oxide and 1 mol of stearyl alcohol. The bath is now warmed from 40° to 97° C. in the course of 30 minutes and is kept at this temperature for 30 minutes and then cooled to 30° C. in the course of 15 minutes. The fabric is then rinsed in running, deionised water and dried at 60° C. The triacetate fabric treated in this manner has a good white effect.

EXAMPLE 10

An acetate satin fabric is treated, on a dyeing apparatus, at a liquor ratio of 1:20, with an aqueous bath containing 0.1%, based on the weight of fabric, of the compound of the formula (101), (103), (202), (301) or (401), 1 g/liter of the condensation product of 35 mols of ethylene oxide and 1 mol of stearyl alcohol, and 0.5 ml/liter of 80% acetic acid. The bath is now warmed from 40° to 80° C. in the course of 30 minutes and is kept at this temperature for 30 minutes and then cooled to 20° C. in the course of 15 minutes. The fabric is then rinsed in running, deionised water and dried at 60° C. The acetate satin fabric treated in this manner is distinguished by a good white effect.

EXAMPLE 11

1,000 g of polyester granules of the ethylene glycol terephthalate type containing 0.5% of $TiO_2$ (anatase type) are mixed with 0.5 g of a compound of the formula (104), (105), (201) or (404) in a gyro-wheel stirrer, and the granules treated in this manner are spun at 280° C. in an extrusion-spinning unit to give multifilament yarn. The filaments formed have an excellent white effect with a good fastness to light.

EXAMPLE 12

100 parts of polystyrene containing about 1.5% of $TiO_2$ (rutile type) are mixed, in the dry state, with 0.05 part of a compound of the formula (104), (105), (201), (202) or (405) and the mixture is processed in an extruder at 180° C. to give whitened granules. The granules are shaped into platelets with the aid of a plunger-type injection moulding machine. The platelets obtained in this manner have a good white effect with good fastness to light.

EXAMPLE 13

An intimate mixture of 65 parts of polyvinyl chloride (suspension type), 32 parts of dioctyl phthalate, 3 parts of an epoxidised soya bean oil, 1.5 parts of a stabiliser, 0.5 part of a costabiliser, 5 parts of $TiO_2$ (rutile type) and 0.05 part of a compound of the formula (201), (403), (404), (405) or (102) are converted to sheeting on a calender at 150° C. The resulting sheeting has a good white effect with good fastness to light.

What is claimed is:

1. A 6-styrylquinoxaline of the formula

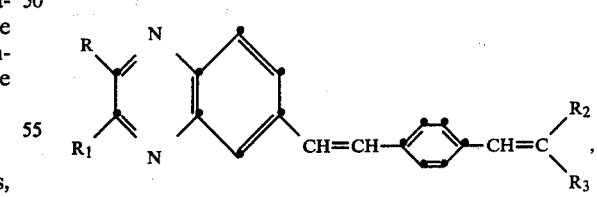

in which R and $R_1$ independently of one another are hydrogen, alkyl, aryl or aryloxy which is unsubstituted or substituted by non-chromophoric substituents, alkoxy, alkoxyalkoxy or phenylthio, $R_2$ is hydrogen or alkyl and $R_3$ is cyano or a group of the formula

in which $R_4$ is alkoxy, alkoxyalkoxy, acyloxyalkoxy,

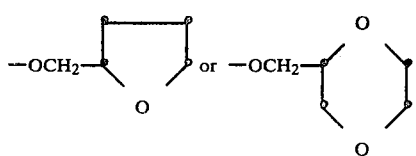

2. A 6-styrylquinoxaline according to claim 1, in which R and $R_1$ independently of one another are aryl or aryloxy which is unsubstituted or substituted by nonchromophoric substituents, or alkoxy, alkoxyalkoxy or phenylthio.

3. A 6-styrylquinoxaline according to claim 2, of the formula

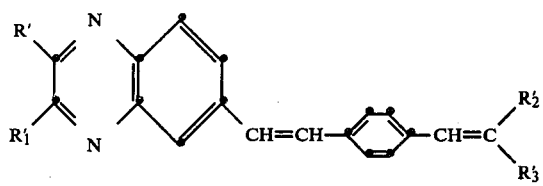

in which R' and $R_1'$ independently of one another are phenyl of phenoxy which is unsubstituted or substituted by one or two substituents from the group comprising halogen and alkyl and alkoxy having in each case 1 to 4 C atoms, or are alkoxy having 1 to 4 C atoms, alkoxyethoxy having 3 to 6 C atoms or phenylthio, $R_2'$ is hydrogen or alkyl having 1 to 4 C atoms and $R_3'$ is cyano or a group of the formula

in which $R_4'$ is alkoxy having 1 to 4 C atoms, alkoxyethoxy having 3 to 6 C atoms, alkanoyloxyethoxy having 4 to 7 C atoms,

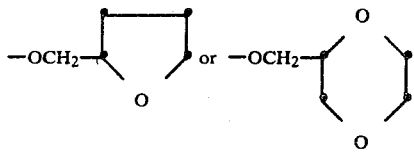

4. A 6-styrylquinoxaline according to claim 3, of the formula

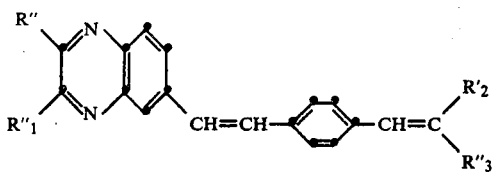

in which R" and $R_1''$ independently of one another are alkoxy having 1 to 4 C atoms, alkoxyethoxy having 3 to 6 C atoms, phenyl or phenoxy, $R_2''$ is hydrogen or alkyl having 1 to 4 C atoms and $R_3''$ is cyano or alkoxycarbonyl having 2 to 5 C atoms.

5. A process for the fluorescent brightening of a synthetic, regenerated man-made or natural organic material of high molecular weight, which comprises incorporating a 6-styrylquinoxaline of the formula defined in claim 1 into the material to be subjected to fluorescent brightening, or applying such a compound to the surface of the said material.

6. A process according to claim 5, wherein 0.001 to 2%, preferably 0.01 to 0.5%, of the brightener, based on the weight of the material to be subjected to fluorescent brightening, is used.

7. A process according to either of claims 5 or 6 for the fluorescent brightening of a polyester.

8. A process according to claim 7, wherein polyester fibre fabric is treated with the particular brightener with the aid of the exhaust method or the pad-thermofix method.

9. A process according to claim 7, wherein the particular brightener is incorporated into a polyester spinning composition and is finely dispersed therein, and the resulting whitened spinning composition is then spun through the customary spinnerets.

10. An organic material of high molecular weight which contains 0.001 to 2%, preferably 0.01 to 0.5%, of one or more 6-styrylquinoxalines of the formula defined in claim 1.

* * * * *